US008282396B2

(12) United States Patent
Chow et al.

(10) Patent No.: US 8,282,396 B2
(45) Date of Patent: *Oct. 9, 2012

(54) CALCIUM-CONTAINING RESTORATION MATERIALS

(75) Inventors: Laurence C. Chow, Germantown, MD (US); Shozo Takagi, Gaithersburg, MD (US)

(73) Assignee: ADA Foundation, Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/772,843

(22) Filed: May 3, 2010

(65) Prior Publication Data

US 2010/0212545 A1 Aug. 26, 2010

Related U.S. Application Data

(60) Division of application No. 10/552,337, filed on Jul. 21, 2006, now Pat. No. 7,709,029, which is a continuation-in-part of application No. 10/057,554, filed on Jan. 23, 2002, now Pat. No. 6,793,725.

(60) Provisional application No. 60/263,894, filed on Jan. 24, 2001, provisional application No. 60/461,338, filed on Apr. 8, 2003.

(30) Foreign Application Priority Data

Mar. 11, 2004 (WO) ............... PCT/US2004/000742

(51) Int. Cl.
*A61C 5/00* (2006.01)
*A61C 5/04* (2006.01)
*C04B 12/02* (2006.01)

(52) U.S. Cl. .................. 433/215; 433/226; 106/690

(58) Field of Classification Search .................. 433/215, 433/226; 106/690
See application file for complete search history.

(56) References Cited

U.S. PATENT DOCUMENTS

| | | |
|---|---|---|
| 3,679,360 A | 7/1972 | Rubin et al. |
| 3,787,900 A | 1/1974 | McGee |
| 3,913,229 A | 10/1975 | Driskell et al. |
| 3,929,971 A | 12/1975 | Roy |
| 4,097,935 A | 7/1978 | Jarcho |
| 4,486,403 A | 12/1984 | Mechanic et al. |
| 4,497,075 A | 2/1985 | Niwa et al. |
| 4,512,038 A | 4/1985 | Alexander et al. |
| 4,518,430 A | 5/1985 | Brown et al. |
| 4,599,085 A | 7/1986 | Riess et al. |
| 4,612,053 A | 9/1986 | Brown et al. |
| 4,655,777 A | 4/1987 | Dunn et al. |
| 4,813,876 A | 3/1989 | Wang |
| 4,880,610 A | 11/1989 | Constantz |
| 4,897,250 A | 1/1990 | Sumita |
| RE33,161 E | 2/1990 | Brown et al. |
| 4,902,649 A | 2/1990 | Kimura et al. |
| RE33,221 E | 5/1990 | Brown et al. |
| 4,963,151 A | 10/1990 | Ducheyne et al. |
| 5,034,059 A | 7/1991 | Constantz et al. |
| 5,037,639 A | 8/1991 | Tung |
| 5,047,031 A | 9/1991 | Constantz et al. |
| 5,053,212 A | 10/1991 | Constantz et al. |
| 5,092,888 A | 3/1992 | Iwamoto et al. |
| 5,129,905 A | 7/1992 | Constantz et al. |
| 5,181,930 A | 1/1993 | Dumbleton et al. |
| 5,192,330 A | 3/1993 | Chang et al. |
| 5,236,456 A | 8/1993 | O'Leary et al. |
| 5,238,491 A | 8/1993 | Sugihara et al. |
| 5,336,264 A | 8/1994 | Constanz et al. |
| 5,455,231 A | 10/1995 | Constantz et al. |
| 5,496,399 A | 3/1996 | Ison et al. |
| 5,508,342 A | 4/1996 | Antonucci et al. |
| 5,522,893 A | 6/1996 | Chow et al. |
| 5,525,148 A | 6/1996 | Chow et al. |
| 5,542,973 A | 8/1996 | Chow et al. |
| 5,545,254 A | 8/1996 | Chow et al. |
| 5,556,687 A | 9/1996 | McMillin |
| 5,652,016 A | 7/1997 | Imura et al. |
| 5,652,056 A | 7/1997 | Pepin |
| 5,695,729 A | 12/1997 | Chow et al. |
| 5,721,049 A | 2/1998 | Marcolongo et al. |
| 5,766,618 A | 6/1998 | Laurencin et al. |
| 5,782,971 A | 7/1998 | Constantz et al. |
| 5,814,681 A | 9/1998 | Hino et al. |
| 5,861,445 A | 1/1999 | Xu et al. |
| 5,962,028 A | 10/1999 | Constantz |
| 5,976,234 A | 11/1999 | Chow et al. |
| 5,997,624 A | 12/1999 | Chow et al. |
| 6,077,989 A | 6/2000 | Kandel et al. |
| 6,136,029 A | 10/2000 | Johnson et al. |

(Continued)

FOREIGN PATENT DOCUMENTS

DE 4016135 5/1989

(Continued)

OTHER PUBLICATIONS

Chow et. al., "Diametral Tensile Strength and Compressive Strength of a Calcium Phosphate Cement: Effect of Applied Pressure" J. Biomed Mater Res, 53: 511-517 (2000).

Freidman, et al., "Hydroxyapatite Cement—Obliteration and Reconstruction of the Cat Frontal Sinus," Arch. of Otolaryngology—Head & Neck Surgery, vol. 117, pp. 385-389 (Apr. 1991).

Briner, et al., "Significance of Enamel Remineralization", J. Dent. Res. 53:239-243 (1974).

Silverstone, "Remineralization Phenomena", Caries Res. 11 (Supp. 1): 59-84 (1977).

(Continued)

*Primary Examiner* — Shuangyi Abu Ali
(74) *Attorney, Agent, or Firm* — Banner & Witcoff, Ltd.

(57) ABSTRACT

A bone or dental implant material in the form of a paste includes a mixture of calcium phosphate and/or calcium-containing powders, liquid glycerol, organic acid and gelling agent. The paste is stable, resistant to washout and will harden upon exposure to water. Physical characteristics of the paste, including consistency, porosity, and hardening time, are controlled by the choice and ratio of constituents.

5 Claims, No Drawings

U.S. PATENT DOCUMENTS

| | | |
|---|---|---|
| 6,207,098 B1 | 3/2001 | Nakanishi et al. |
| 6,214,008 B1 | 4/2001 | Illi |
| 6,281,256 B1 | 8/2001 | Harris et al. |
| 6,281,257 B1 | 8/2001 | Ma et al. |
| 6,287,341 B1 | 9/2001 | Lee et al. |
| 6,325,992 B1 | 12/2001 | Chow et al. |
| 6,334,775 B2 | 1/2002 | Xu et al. |
| 6,399,350 B1 | 6/2002 | Rubin et al. |
| 6,693,143 B2 | 2/2004 | Pflug |
| 6,793,725 B2 | 9/2004 | Chow et al. |
| 6,949,251 B2 | 9/2005 | Dalal et al. |
| 7,018,460 B2 | 3/2006 | Xu et al. |
| 7,632,878 B2 | 12/2009 | Xu et al. |
| 7,709,029 B2 | 5/2010 | Chow et al. |
| 2002/0137812 A1 | 9/2002 | Chow et al. |
| 2002/0156152 A1 | 10/2002 | Zhang et al. |
| 2003/0147956 A1 | 8/2003 | Shefer et al. |
| 2003/0167093 A1 | 9/2003 | Xu et al. |
| 2003/0181541 A1 | 9/2003 | Wu et al. |
| 2004/0086446 A1 | 5/2004 | Jia et al. |
| 2005/0020720 A1 | 1/2005 | Dickens et al. |
| 2005/0260269 A1 | 11/2005 | Engelbrecht et al. |

FOREIGN PATENT DOCUMENTS

| | | |
|---|---|---|
| EP | 0416761 | 3/1991 |
| EP | 0520690 | * 12/1992 |
| EP | 0538913 | 4/1993 |
| EP | 0639366 | 2/1995 |
| JP | 62275007 | 11/1987 |
| JP | 6429266 | 1/1989 |
| JP | 1301543 | 12/1989 |
| JP | 2311406 | 12/1990 |
| JP | 3183605 | 8/1991 |
| JP | 3193615 | 8/1991 |
| JP | 459611 | 2/1992 |
| JP | 408157658 | 6/1996 |
| JP | 02311406 | * 12/1997 |
| JP | 2001170161 | 6/2001 |
| WO | 9503369 | 1/1989 |

OTHER PUBLICATIONS

Brown, Solubilities of Phosphates and Other Sparingly Soluble Compounds, from Griffith, et al., Environmental Phosphorous Handbook (John Wiley & Sons, New York 1973).

Miyazaki, et al., "An Infrared Spectroscopic Study of Cement Formation of Polymeric Calcium Phosphate Cement," Journal of Japanese Society for Dental Materials and Devices, vol. II, No. 2, 1992.

Brown, et al., "Crystallography of Tetracalcium Phosphate," J. Res. Nat. Bur. Stands. 69A: 547-551, 1965.

Brown and Chow, "Singular Points in the Chemistry of Teeth," IADR Abstract No. 120, J. Dent. Res. 54: 74 (1975).

Driskell, et al., "Development of Ceramic and Ceramic Composite Devices for Maxillofacial Application", J. Biomed. Mat. Res. 6: 345-361 (1972).

Gelhard et al, "Rehardening of Artificial Enamel Lesions in Vivo", Caries Res. 13: 80-83 (1979).

Gregory, et. al., "Solubility of $CaHPO_4 2H_2O$ in the System $Ca(OH)_2$—$H_3PO_4$—$H_2O$ at 5, 15, 25, and 37.5 o C," J. Res. Nat. Bur. Stand, 74A: 461-475 (1970).

Gregory, et. al., "Solubility of—$Ca_3(PO_4)_2$ in the System $Ca(OH)_2$—$H_3PO_4$—$H_2O$ at 5, 15, 25 and 37 C," J. Res. Nat. Bur. Stand. 78A: 667-674 (1974).

Hiatt, et al., "Root Preparation I. Obturation of Dentinal Tubules in Treatment of Root Hypersensitivity", J. Periodontal 43: 373-380 (1972).

Levine, "Remineralization of Natural Carious Lesions of Enamel in vitro," Brit. Dent. J., 137: 132-134 (1974).

McDowell, et al., "Solubility of—$Ca_5(PO_4)_3$ in the System $Ca(OH)_2$—$H_3PO_4$—$H_2O$ at 5, 15, 25 and 37 C," J. Res. Nat. Bur. Stand. 81A:273-281 (1977).

McDowell, et al., "Solubility Study of Calcium Hydrogen Phosphate. Ion Pair Formation," Inorg. Chem. 10:1638-1643 (1971).

Moreno, et al., "Stability of Dicalcium Phosphate Dihydrate in Aqueous Solutions and Solubility of Octacalcium Phosphate," Soil Sci. Soc. Am. Proc. 21: 99-102 (1960).

Patel, et al., "Solubility of $CaHPO_4 2H_2O$ in the Quaternary System $Ca(OH)_2$—$H_3PO_4$—NaCl—$H_2O$ at 25 C," J. Res. Nat. Bur. Stands. 78A: 675-681 (1974).

Picket, et al. "The Effect of a Chewing Gum Containing Dicalcium Phosphate on Salivary Calcium and Phosphate", Ala. J. Med. Sci. 2: 286-287.

Zimmerman, et. al., "The Effect of Remineralization Fluids on Carious Lesions in Vitro," IADR Abstract No. 282 (1979).

Guide to Dental Materials and Devices, 7th Ed. (ADA 1974) pp. 49-64.

Brown, et al., (1988): "A New Calcium Phosphate, Water Setting Cement," Cements Research Progress 1986, P.W. Brown, Ed., Westerville, Ohio: American Ceramic Society, pp. 352-379.

Chohayeb, A.A., et al., (1987): Evaluation of Calcium Phosphate as a Root Canal Sealer-Filler Material, J. Endod 13, 384-386.

Hong, et al., (1989): The Periapical Tissue Reactions to a Calcium Phosphate Cement in the Teeth of Monkeys, J. Dent Res (submitted).

Constantino, et al. (1989): Evaluation of a New Hydroxyapatite Cement: Cranioplasty in a Cat Model, The Fifth International Symposium on Facial Plastic Reconstructive Surgery of the Head and Neck, Toronto, Canada.

De Rijk, et al. (1986): Clinical Evaluation of an Hydroxyapatite Precipitate for the Treatment of Dentinal Hypersensitivity, Biomedical Engineering V. Recent Developments, Proc of 5th Southern Biomedical Engineering Conference, Subrata Saha, Ed., New York: Pergamon Press, pp. 336-339.

Grunninger et al, (1984): Evaluation of the Biocompatibility of a New Calcium Phosphate Setting Cement, J. Dent Res., 63 (Special Issue) Abst. No. 270.

Hanker et. al, (1987): Calcium Phosphate Bindrs for Hydroxyapatite Particles for Bone Reapir, J. Dent Res. 66, Abst. No. 1144.

Lu, et al, (1988): New Attachment Following the Use of a Novel Calcium Phosphate System, J. Dent Res. Res 67: 352, Abst. No. 1913.

Schreiber, et. al., (1988): Remineralizaton of Root Caries Lesion by a Calcium Phosphate Slurry, J. Dent Res. 67: Abst. No. 255.

Sugawara, et. al, (1987): A Calcium Phosphate Root Canal Sealer-Filler, J. Dent Res. 66: 296 Abst. No. 1516.

Sugawara et al (1989): Formation of Hydroxyapatite in Hydrogels from Tetracalcium Phosphate/Dicalcium Phosphate Mixtures, Nihon Univ. Sch. Dent., vol. 31, No. 1, 372-81, 1989.

Block, et al. (1988): Correction of Vertical Orbital Dystopia with a Hydroxyapatite Orbital Floor Graft, J. Oral Maxillofac Surg 46: 420-425, 1988.

Salyer, et al. (1989): Porous Hydroxyapatite as an Onlay Bone-Graft Substitute for Maxillofacial Surgery, Plas and Recon Surg 84, 2:236-244, 1989.

Kenney, et al. (1988): The Use of a Porous Hydroxyapatite Implant in Periodontal Defects, J. Periodontal, pp. 67-72 Feb. 1988.

Zide et al (1987): Hydroxyapatite Cranioplasty Directly Over Dura, J. Oral Maxillofac Surg 45:481-486, 1987.

Waite, et al. (1986): Zygomatic Augmentation with Hydroxyapatite, J. Oral Maxillofac Surg 44:349-352, 1986.

Verwoerd, et al. (1987): Porous Hydroxyapatite-perichondrium Graft in Cricoid Reconstruction, Acta Otolaryngol (Stockh) 1987; 103:496-502.

Grote, (1984): Tympanoplasty With Calcium Phosphate, Arch Otolaryngology 110:197-199, 1984.

Kent, et al. (1983): Alveolar Ridge Augmentation Using Nonresorbable Hydroxyapatite With or Without Autogenous Cancellous Bone, J. Oral Maxillofac Surg 41:629-642, 1983.

Piecuch (1986): Augmentation of the Atrophic Edentulous Ridge with Porous Replamineform Hydroxyapatite (Interpore-200), Dental Clinics of North America 30, 2:291-305, 1986.

Misch (1987): Maxillary Sinus Augmentation for Endosteal Implants: Organized Alternative Treatment Plans, Int J Oral Implant 4, 2:49-58, 1987.

Chow, L.C., "Calcium Phosphate Materials: Reactor Response" Adv Dent Res 2(1): 191-184, Aug. 1988.

Fukase, et al., "Setting Reactions and Compressive Strengths of Calcium Phosphate Cements", J Dent Res 69 (12):1852-1856, Dec. 1990.

Chow, et al., "Self-Setting Calcium Phosphate Cements," Mat. Res. Soc. Symp. Proc. vol. 179, 1991.
Miyazaki, et al. "Chemical Change of Hardened PCA/CPC Cements in Various Storing Solutions," The Journal of the Japanese Soc. for Den. Mats. and Devices, vol. 11, No. 2, 1992.
Fukase et al, "Thermal Conductivity of Calcium Phosphate Cement," IADR Abstract, 1990.
Constantino, et al., "Hydroxyapatite Cement—Basic Chemistry and Histologic Properties," Arch. of Otolaryngology—Head & Neck Surgery, vol. 117, pp. 379-384 (Apr. 1991).
Mirtchi, et al., "Calcium phosphate cements: study of the β-tricalcium phosphate-monocalcium phosphate system," Biomaterials, vol. 10, pp. 475-480 (1989).
Mirtchi, et al, "Calcium phosphate cements: study of the β-tricalcium phosphate-dicalcium phosphate-calcite cements," Biomaterials, vol. 11, pp. 83-88 (1990).
Mirtchi, et al., "Calcium phosphate cements: effect of fluorides on the setting and hardening of β-tricalcium phosphate-dicalcium phosphate-calcite cements," Biomaterials, vol. 12, pp. 505-510 (1991).
Fulmer, et al. "Effects of Na2 HPO4 and NaH2PO4 on Hydroxyapatite Formation," J. Biomed. Mat. Res., vol. 27, pp. 1095-1102 (1993).
Ishikawa, et al., "The Hydrolysis of Anhydrous Dicalcium Phosphate into Hydroxyapatite," J. of Dent. Res., vol. 72, No. 2, pp. 474-480 (Feb. 1993).
Sugawara, et al., "In Vitro Evaluation of the Sealing Ability of a Calcium Phosphate Cement When Used 5s a Root Canal Sealer-Filler," J. of Endodontics, vol. 16, No. 4, pp. 162-165 (1990).
Shindo, et al., "Facial Skeletal Augmentation Using Hydroxyapatite Cement," Arch. of Otolaryngology—Head & Neck Surgery, vol. 119, pp. 185-190 (Feb. 1993).
Constantino, et al., "Experimental Hydroxyapatite Cement Cranioplasty," (Aug. 1992).
Sanin, et al., K. Ishikawa, S. Takagi, L.C. Chow and E.D. Eanes, "Effects of Additives on Setting Reaction of Calcium Phosphate Cement," IADR Abstr. #666 J. Dent Res. 71 189 (1992).
Driessens, et al., 1993, "New Apatite Calcium Phosphate Bone Cement: Preliminary Results," in Bioceramics (Ducheyne & Christiansen, eds.) Butterworth-Heinemann Ltd., vol. 6, pp. 469-473.
Miyazaki, et al., 1993, "Polymeric calcium phosphae cements: analysis of reaction products and properties," Dent. Mater. 9:41-45.
Miyazaki et al, 1993, "Polymeric calcium phosphate cements: setting reaction modifiers," Dent Mater. 9:46-50.
Chow et al., 1994, "Formulation of Hydroxyapatite in Cement Systems," in Hydroxyapatite and Related Materials (Brown & Constanz, eds.), CRC Press: Boca Raton, FL pp. 127-137.
Constantz, et al., 1995, "Skeletal Repair by Situ Formation of the Mineral Phase of Bone," Science 267: 1796-1798.
Chow and Takagi, 1995, "Rate of Dissolution of Calcium Phosphate Cements," J. Dent. Res. 74:537 (IADR Abstract #1094).
Takagi and Chow, 1995, "Formation of Macropores in Calcium Phosphate Cement Implants," J. Dent. Res. 74:537 (IADR Abstract #1272).
Horioglu, et al., 1995, "Composite Implant of Hydroxyapatite Cement/Osteogenic Protein-1 In Experimental Cranial Construction: Preliminary Results," Transactions of the 21st Annual Meeting for the Society for Biomaterials, San Francisco, CA, Mar. 18-22, p. 72.
Driessens, et al., 1995, "Effective formulations for the preparation of calcium phosphate bone cements," J. Mater.Sci.: Mater.Med. 5:164-170.
Fernandez, et al., 1994, "Common Ion Effect on some Calcium Phosphate Cements," Clinial Mater.16:99-103.
Matsuya, et al., 1994, Formation of Hydroxyapatitein a Polymeric Calcium Phosphate Cement, Proc. Int. Conf. Comp. Eng.
Bermudez, et al., Optimization of Calcium Orthophosphae Cement formulation occurring in the combination of monocalcium phosphate monohydrate with calcium oxide, J. Mater.SciMater Med 5:67-71.
Dickens-Venz, et. al., 1994, "Physical and chemical properties of resin-reinforced calcium phosphate cements," Dent. Mater.10:100-106.
LeGeros, et al., "Apatitic Calcium Phosphates: Possible Dental Restorative Materials", IADR Abstract No. 1482 J. Dent Res. (1982).
"NASA and Dentistry" (1977).

Chow, "Development of Self-Setting Calcium Phosphate Cements," Journal of the Ceramic Society of Japan, 99[10] 954-964 (1991).
Sugawara, et al., "Biocompatibility and Osteoconductivity of Calcium Phosphate Cement" IADR Abstract (1990).
Miyazaki et al., "Polymeric Calcium Phosphate Cements", IADR Abstract (1990).
Sugawara et al., "Histopathological Reactions of a Calcium Phosphate Cement Root Canal Filler", IADR Abstract (1991).
Sanin et al., "Particle Size Effects on pH and Strength of Calcium Phosphate Cement", IADR Abstract (1991).
Link et al., "Composite of Calcium Phosphate Cement and Genetically Engineered Protein Bioadhesive", IADR Abstract (1991).
Matsuya et al., "Effects of pH on the Reactions of Tetracalcium Phosphate and Dicalcium Phosphate", IADR Abstract (1991).
Chow et al., "X-ray Diffraction and Electron Microscopic Characterization of Calcium Phosphate Cement Setting Reactions", IADR Abstract (1987).
Sugawara et al., "An in Vitro Study of Dentin Hypersensitivity Using Calcium Phosphate Cement", Jour of Jap. Soc. For Dent. Mats & Devices, vol. 8, No. 2, 1989.
Mirtchi et al., "Calcium Phosphate Cements: Action of Setting Regulars on the Properties of the β-tricalcium Phosphate-Monocalcium Phosphate Cements" Biomaterials, vol. 10, pp. 634-638 (1989).
Cherng et al., 1995, Effects of Gelling Agents on Calcium Phosphate Cements, J. Dent. Res. 74:242 (IADR Abstract, No. 1845).
Horioglu et al., 1995, "Long-Term Follow-Up of Hydroxyapatite Cement (HAC) Implant for Craniofacial Construction", Transactions of the 21st Annual Meeting for the Society of Biomaterials, San Francisco, CA, Mar. 18-22, p. 198.
Fujikawa et al., 1995, "Histopathological Reaction of Calcium Phosphate Cement in Periodontal Bone Defect", Dent. Mater. J. 10:45-57.
Sugawara et al., 1995, "Histopathological Reaction of Calcium Phosphate Cement Root Canal Filler", J. Hard Tissue Biology, 4:1-7.
Chow, "Calcium Phosphate Cements: Chemistry, Properties and Applications", Mat. Res. Soc. Sump. Proc., vol. 599, 2000.
Takagi et al., Formation of Macropores in Calcium Phosphate Cement Implants, J. Mat. Sci: Materials in Medicine, 12 (2001) 135-139.
Grozier, "New Cement Makes Medical History", ADA News, Jan. 4, 1993; vol. 24, No. 1.
Shors et al., "Porous Hydroxyapatite", An Introduction to Bioceramics, pp. 181-198.
Fukase et al., "Setting Reactions and Compressive Strengths of Calcium Phosphate Cements", J Dent Res 69 (12): 1852, Dec. 1990.
Matsuya et al., Effect of Fluoride on Apatite Formation From Ca4(PO4)20 in 0.1 mol L-1 KH2PO4, J Mat. Sci: Materials in Medicine 9 (1998) pp. 325-331.
Chang et al., "Osteoconduction at Porous Hydroxyapatite with Various Pore Configurations", Biomaterials 21 (2000) 1291-1298.
Chow et al., "Calcium Phosphate Cements", Cements Research Progress, 1999, pp. 215-238.
Xu et al., "Calcium Phosphate Cement Containing Resorbable Fibers for Short-Term Reinforcement and Macroporosity", Biomaterials 0 (2001) 1-10.
Xu et al., "Strong and Macroporous Calcium Phosphate Cement: Effects of Porosity and Fiber Reinforcement on Mechanical Properties", Macroporous Calcium Phosphate Cement, pp. 1-10.
Von Gonten et al., "Load-Bearing Behavior of a Simulated Craniofacial Structure Fabricated From a Hydroxyapatite Cement and Bioresorbable Fiber-Mesh" J. Mater. Sci.: Materials in Medicine, 11 (2000) 95-100.
Xu et al., "Effects of Fiber Length and Volume Fraction on the Reinforcement of Calcium Phosphate Cement", J. Mater. Sci: Materials in Medicine, 12 (2001) 57-65.
Xu et al., "Reinforcement of a Self-Setting Calcium Phosphate Cement with Different Fibers", Journal of Biomedical Materials Research, Oct. 2000, vol. 51, No. 1, pp. 107-114.
Suchanek et al., "Processing and Properties of Hydroxyapatite-Based Biomaterials for use as Hard Tissue Replacement Implants", J. Mater. Res., vol. 13, No. 1, Jan. 1998, pp. 94-117.
Simske, et al., "Porous Materials for Bone Engineering", Materials Science Forum, vol. 250 (1997) pp. 151-182.

LeGeros, "Biodegradation and Bioresorption of Calcium Phosphate Ceramics", Clinical Materials, 14 (1993) pp. 65-88.

Friedman et al., "BoneSource Hydroxyapatite Cement: A Novel Biomaterial for Craniofacial Skeletal Tissue Engineering and Reconstruction", Hac for Tissue Engineering and Reconstruction, pp. 428-432.

Takagi et al., "Morphological and Phase Characterizations of Retrieved Calcium Phosphate Cement Implants", 2000, pp. 36-41.

Ishikawa et al., "Reaction of Calcium Phosphate Cements With Different Amounts of Tetracalcium Phosphate and Dicalcium Phosphate Anhydrous", CPC With Different TTCP/DCPA Molar Ratios, pp. 504-510.

Miyamoto et al., "Histological and Compositional Evaluations of Three Types of Calcium Phosphate Cements When Implanting in Subcutaneous Tissue Immediately After Mixing", Three CPCs in Soft Tissue, 1999, pp. 36-42.

Constantz et al., "Histological, Chemical, and Crystallographic Analysis of Four Calcium Phosphate Cements in Different Rabbit Osseous Sites", Calcium Phosphate Cements, 1998, pp. 451-461.

Ginebra et al., "Setting Reaction and Hardening of an Apatitic Calcium Phosphate Cement", J. Dent. Res., 76 (4): 905-912, Apr. 1997.

Posner et al. "Synthetic Amorphous Calcium Phosphate and Its Relation to Bone Mineral Structure", Accounts of Chemical Research, 8, 273 (1975).

de Groot, "Ceramics of Calcium Phosphates: Preparation and Properties", Bioceramics of Calcium Phosphate, pp. 99-114.

Blumenthal, et al., "Effect of Preparation Conditions on the Properties and Transformation of Amorphous Calcium Phosphate", Mat. Res. Bull. 7:1181-1190 (1972).

Aoba, "X-Ray Diffraction Study on the Amorphous and Crystalline Components in Bone Mineral", Chem. Abstracts, vol. 91, No. 13 Abstract No. 105935r, (1979).

Aoba et al., "Small Angle X-Ray Scattering Study on the Transformation of Amorphous Calcium Phosphate to Crystalline Apatite," Chem. Abstracts, vol. 91, No. 13, Abstract No. 105934q (1979).

Tung et al., "Hydrolysis of Dicalcium Phosphate Dihydrate in the Presence or Absence of Calcium Fluoride", Basic Biological Sciences Dent. J. Res. 64(1): Jan. 2-5, 1985.

Tung et al., "An Intermediate State in Hydrolysis of Amorphous Calcium Phosphate", Calcified Tissue International, 783-790 (1983).

Tung, et al., "The Effects of Calcium Phosphate Solutions on Permeability of Dentin" J. Dent. Res., 65 Abstract No. 167 (1986).

Tung et al., "Effects of Calcium Phosphate Solutions on Dentin Permeability", vol. 19, No. 8 J of Endodontic (1983).

Trautz, "Crystallographic Studies of Calcium Carbonate phosphate" Annals of the N.Y. Acad. Sci. 35, Article 1: 145-160 (1960).

Termine et al., "Calcium Phosphate in vitro", Chem. Abstracts, vol. 73, Abstract No. 126985a, (1970).

Yasue et al, "Synthesis and Characteristics of Amorphous Calcium Carbonate in Ethanol", Fac. Sci Eng., Nihon Univ. Gypsum Lime, 1985, 198 245-52 Japan.

Bowen et al., "Development of an Adhesive Bonding System", Operative Dentistry, Supplement 5, 1992, pp. 75-80.

Yu et al., "Self-Setting Hydroxyapatite Cement: A Novel Skeletal Drug-Delivery System for Antibiotic", J. Pharm. Sci., vol. 81, No. 6, Jun. 1992, pp. 529-531.

* cited by examiner

CALCIUM-CONTAINING RESTORATION MATERIALS

CROSS REFERENCE TO RELATED APPLICATIONS

This application is a divisional application based upon and claiming priority to and incorporating by reference Ser. No. 10/552,337 filed Jul. 21, 2006 now U.S. Pat. No. 7,709,029 entitled "Calcium Containing Restoration Materials" which is a U.S. national stage under 35 USC 371 and is a continuation in part of U.S. application Ser. No. 10/057,554, filed Jan. 23, 2002, now U.S. Pat. No. 6,793,725 which claims the benefit of U.S. Provisional Patent Application Ser. No. 60/263,894, filed on Jan. 24, 2001. Ser. No. 10/552,337 also claims the benefit of U.S. Provisional Patent Application Ser. No. 60/461,338, filed on Apr. 8, 2003, all of which are incorporated herein by reference and for which priority is claimed.

STATEMENT REGARDING FEDERALLY SPONSORED RESEARCH OR DEVELOPMENT

This development was supported in part by USPHS, Research Grant DE11789 to the American Dental Association Health Foundation from the NIDCR. The United States or an agency thereof may have certain rights to the claimed invention

BACKGROUND OF THE INVENTION

The various embodiments of the present invention are generally directed to self-hardening calcium phosphate-containing and/or calcium-containing cement compositions. The compositions may be used to form pastes for bone and tooth restoration and similar applications, where the paste will harden within a desired time after being delivered to a repair site.

Most conventional calcium phosphate cements are mixed with an aqueous solution immediately before application. In the clinical situation, the ability of the surgeon to properly mix the cement and then place the cement paste in the defect within the prescribed time is a crucial factor in achieving optimum results A self-hardening calcium phosphate cement ("CPC"), consisting of tetracalcium phosphate ($Ca_4(PO_4)_2O$, also referred to as "TTCP") and dicalcium phosphate anhydrous ($CaHPO_4$, also referred to as "DCPA"), has been shown in clinical studies to be efficacious for repairing bone defects. The hardening time of such conventional cements is as long as about 30 minutes with water, although hardening time can be shortened if a phosphate solution is used as the cement liquid. Hydroxyapatite ($Ca_5(PO_4)_3OH$, also referred to as "HA") is formed as the product. More recently, additional CPCs that do not contain TTCP, e.g., α-tricalcium.phosphate (α-$Ca_3(PO_4)_2$, also referred to as "α-TCP") and $CaCO_3$ or DCPA and $Ca(OH)_2$, have also been developed. These cements may harden in about 10 minutes when a phosphate solution is used as the cement liquid. They also form hydroxyapatite ("HA") as the final product.

A premixed CPC paste containing the TTCP and DCPA powders and glycerol as the cement liquid has been used for root canal filling and sealing by injection techniques. The cement paste was found to be stable in a syringe but hardened only after being delivered into the root canal where it became exposed to water from the surrounding tissues. Because the cement paste was injected into a confined area, there was little concern of disintegration of the paste due to washout. Although the premixed CPC was shown to have improved biocompatibility with periapical bone tissue than a number of conventional root canal filling or sealing materials, the premixed CPC-glycerol paste did not exhibit a good washout resistance when it was applied to an open wet field.

There remains a need for premixed cement pastes that are stable in the package, are resistant to washout, and will harden only after being deposited at the site of the defect but, once placed, will then harden within a predetermined time.

BRIEF SUMMARY OF THE INVENTION

The various embodiments of the present invention comprise compositions and means for formulating premixed calcium and/or calcium phosphate and organic acid cement pastes that are stable in a package, resistant to washout, and harden within a desired time after being delivered to the defect or implant site. A non-toxic, non-aqueous, water-miscible liquid such as glycerol is preferred as the liquid in the premix because the cement paste hardening reaction to form calcium complexes and HA does not occur in a water-free environment. An organic acid is used to accelerate cement hardening upon delivery to a desired repair site. Preferred organic acids include carboxylic acids. A gelling agent also may be added to improve the paste cohesiveness.

Methods of repairing and restoring bone and tooth tissue include delivering the pastes to the defect site by any suitable methods known to those of skill in the art. The pastes are exposed to an aqueous fluid to promote hardening of the paste to a cement at a relatively rapid rate.

When premixed self-hardening cements are formulated with sodium phosphate ("$Na_2HPO_4$") to accelerate cement hardening and prepared by mixing glycerol, $Na_2HPO_4$, and hydroxypropyl methyl cellulose ("HMC") with CPC powders, the cements will harden only after being delivered to a desired site. Although $Na_2HPO_4$ may serve to accelerate cement hardening, the hardening times ("HT") of these cements can be 60 minutes or longer. Where shorter hardening times are desired, the present compositions that include organic acids to accelerate cement hardening provide self-hardening calcium phosphate-containing and/or calcium-containing cement pastes having hardening times of about 35 minutes or less.

Thus, it is an object of the invention to provide a premixed composition of a calcium phosphate-containing and/or calcium-containing cement material which exhibits resistance to washout as well as desirable hardening times.

A further object of the invention is to provide an essentially water-free, cement-forming paste capable of forming calcium complexes and HA after exposure to water for repair of dental material and bone.

Another object of the invention is to provide a method for controlling the hardening times of HA forming cements pastes.

Another object of the invention is to provide an HA forming cement formulation capable of remaining in an injectable paste form until exposed to an aqueous environment.

These and other objects, advantages and features of the invention are set forth in the detailed description which follows.

DETAILED DESCRIPTION OF THE INVENTION

Premixed calcium cement pastes for use in bone graft and similar medical repair applications are provided. The pastes may be injectable for delivery to the bone or tooth defect site. The pastes may include a non-toxic, calcium-containing and/ or calcium phosphate-containing powder, a non-toxic organic acid capable of forming calcium complexes, and a non-toxic, non-aqueous, water-miscible liquid. Non-aqueous liquids are preferred to limit premature hardening of the pastes, which may harden in aqueous environments. A preferred liquid is glycerin (also sometimes referred to as "glycerol"). The organic acid is used to accelerate the hardening time of the paste upon delivery. Gelling agents, such as HMC, carboxymethyl cellulose ("CMC"), alginate, chitosan, and the like, also can be mixed with the powders to enhance paste cohesiveness and washout resistance.

Because the hardening of these cements results from calcium-complex formation, it is contemplated that self-hardening cements can also be formulated using calcium-containing compounds instead of, or in combination with, calcium phosphate compounds. The calcium phosphate and/or calcium-containing compound powder can include monocalcium phosphate monohydrate ("MCPM"), mono calcium phosphate anhydrous ("MCPA"), dicalcium phosphate anhydrous ("DCPA"), dicalcium.phosphate dehydrate ("DCPD"), octacalcium phosphate ("OCP"), α-TCP, β-tricalcium phosphate ("β-TCP"), amorphous calcium phosphate ("ACP"), calcium deficient HA, non-stoichiometric HA, TTCP, $CaSO_4$, $CaSO_4.0.5H_2O$, $CaSO_4.2H_2O$, CaO, $Ca(OH)_2$, and $CaCO_3$ and combinations thereof. Preferred calcium phosphate powders include TTCP, DCPA, α-TCP and β-TCP. The Ca/P molar ratio of TTCP is preferably between about 1.67 to about 2, of α-TCP is between about 1.5 to about 1.67, and of β-TCP is between about 1.50 to about 1.67. The particle sizes of the calcium phosphate and/or calcium-containing compounds are between about 1 to about 200 μm and more preferably between about 2 to about 50 μm.

Any suitable, non-toxic, non-aqueous, water-miscible liquid may be used in preparing the pastes. Possible liquids include glycerin, as well as related liquids, such as glycerin compounds, derivatives, substitutes and the like, that are non-toxic, non-aqueous, and water-miscible. Certain alcohols also may be suitable for use as the non-toxic, non-aqueous, water-miscible liquid. Preferably, the liquid is selected from glycerin, propylene glycol, poly(propylene glycol), poly(ethylene glycol), and combinations thereof.

Preferred organic acids are non-toxic, organic carboxylic acids. A number of carboxylic acids form calcium complexes that are not highly soluble. These acids include glycolic, citric, tartaric, malonic, malic, and maleic acids. Some of these acids, when mixed with a powder containing one or more of calcium phosphate compounds and/or calcium-containing compounds produce relatively fast hardening cements. Thus, it is possible that the use of these acids can produce faster setting premixed cements. One or more of these acids are mixed with the powder to provide a stable paste that will harden only upon contact with an aqueous fluid. Without wishing to be bound by any theories, it is believed that the calcium phosphate compounds and/or calcium-containing compounds react with the organic acids in the presence of water to initially form calcium complexes that are not highly soluble, rather than to directly form hydroxyapatite. This then results in more rapid hardening of the paste.

The compositions also may include a non-toxic gelling agent to enhance paste cohesiveness and washout resistance. The gelling agent may include HMC, CMC, chitosan, collagen, gum, gelatin, and alginate, and combinations thereof.

The compositions are prepared and stored under substantially anhydrous conditions to limit premature hardening of the cement pastes. The compositions may be employed as self-hardening cement pastes in a variety of medical and dental procedures for repairing or restoring missing or defective bone or tooth tissue. The cement pastes may be applied to the defect site using any suitable methods, including injecting with a syringe or depositing with a spatula, and also molded or sculpted in vivo as desired. When the cement pastes are exposed to physiologic fluids, which contain water, or another aqueous environment at the defect site, they will harden relatively rapidly. An aqueous fluid may be contacted with the compositions either prior to or after application of the cement pastes at the defect site to enhance the rate of hardening of the cement pastes. As an example, a sodium phosphate or saline solution may be sprayed over the surface of the cement paste after it is delivered to the defect site to promote hardening of the outer surface of the cement paste, which will also assist with maintaining the shape of the cement paste as applied and molded. As another example, water may be mixed with the cement pastes prior to application of the pastes at the defect site to initiate hardening.

For most clinical applications, a cement hardening time of more than 60 minutes is too long. Premixed pastes or self-hardening bone graft pastes ("BGPs") in accordance with the various embodiments of the present invention will have an HT of no more than about 35 minutes, preferably no more than 20 minutes and even more preferably between about 5 to about 15 minutes.

EXAMPLES

The following examples further illustrate preferred embodiments of the present invention but are not be construed as in any way limiting the scope of the present invention as set forth in the appended claims.

Various premixed self-hardening pastes were prepared. Hardening times and other properties of the pastes were evaluated.

Preparation of the solid ingredients of premixed paste: TTCP was prepared by heating an equimolar mixture of commercially obtained DCPA (Baker Analytical Reagents, J.T. Baker Chemical Co., Phillipsburg, N.J.) and $CaCO_3$ (J.T. Baker Chemical Co.) at 1500° C. for 6 hours in a furnace and quenched at room temperature. The TTCP and DCPA powders of the paste compositions were ground individually in a planetary ball mill in cyclohexane, ethanol, or without a liquid to obtain the desired median particle sizes, which typically is about 15 μm as disclosed in the prior art for making CPC powders. The median particle sizes of TTCP and DCPA were about 17.1 μm and about 1.7 μm, respectively.

α-TCP was prepared by heating a mixture that contained 2 mol of DCPA and 1 mol of $CaCO_3$ to 1500° C. for 6 hours and then quenched in air. The powders were ground individually in a planetary ball mill in cyclohexane, ethanol, or without a liquid to obtain the desired median particle sizes based on data from previous studies. The median particle sizes of α-TCP and $CaCO_3$ were 4.6 and 3.9 μm, respectively. The median particle size of $Ca(OH)_2$ was 2.2 μm. The particle sizes of the components of the pastes prepared in accordance with the present invention generally can be in the range of 1 to 50 μm.

Liquid ingredients of controls and premixed pastes: All ingredients were obtained commercially. A homogeneous mixture of a carboxylic acid, HMC or CMC, and glycerin was produced by blending the mixture in a ball mill.

Preparation of premixed pastes: Premixed paste compositions were prepared by mixing a powder and a liquid at desired powder-to-liquid mass ratios (P/L) on a mixing block until a smooth and homogenous paste was obtained. The compositions, with components expressed in mass fraction (%) are presented in Table 1.

TABLE 1

| Paste | Solid | Liquid Glycerin | Liquid Carboxylic Acid | Liquid Gelling Agent | P/L |
|---|---|---|---|---|---|
| P1 | TTCP (73%) DCPA (27%) | 62.2% | d-tartaric acid (37.5%) | HMC (0.3%) | 3.0 |
| P2 | TTCP (73%) DCPA (27%) | 62.2% | glycolic acid (37.5%) | HMC (0.3%) | 3.0 |
| P3 | TTCP (73%) DCPA (27%) | 70.5% | malonic acid (29%) | HMC (0.5%) | 3.0 |
| P4 | TTCP (73%) DCPA (27%) | 79.5% | maleic acid (20%) | HMC (0.5%) | 3.0 |
| P5 | TTCP (73%) DCPA (27%) | 49.3% | citric acid (49.2%) | CMC (1.5%) | 2.3 |
| P6 | TTCP (39.1%) α-TCP (60.9%) | 61.9% | d-tataric acid (37.1%) | CMC (1%) | 1.5 |
| P7 | TTCP (55%) DCPA (20%) α-TCP (25%) | 61.9% | d-tataric acid (37.1%) | CMC (1%) | 1.5 |
| P8 | TTCP | 61.9% | d-tataric acid (37.1%) | CMC (1%) | 1.5 |
| P9 | α-TCP | 61.9% | d-tataric acid (37.1%) | CMC (1%) | 1.5 |

Washout resistance test: The washout resistance of the premixed pastes was tested as follows. Premixed paste samples were shaped into a small sphere by hand, and then placed immediately in a 5 mL of physiologic-like solution ("PLS") (1.15 mM Ca, 1.2 mM P, 133 mM NaCl, 50 mM HEPES, pH=7.4) at 37° C. The sample was considered to pass the washout resistance test if it did not visibly disintegrate in the PLS. All samples exhibited excellent washout resistance.

Diametral tensile strength ("DTS") measurement: DTS samples were prepared by placing the premixed paste into a mold (6 mm diameter by 3 mm height) with about 2 MPa of applied pressure. The mold was covered with two fritted glass slides (pore size of about 40 μm to about 60 μm, thickness of about 3.5 mm) and immersed in PLS at 37° C. Glycerol-PLS exchange occurred through the fritted glass, allowing the paste to harden. Samples were removed from molds at about 4 hours, and then each sample was immersed in 30 mL of PLS for an additional 20 hours. In some cases, additional samples were prepared and samples were immersed in PLS for an additional 6 days with the PLS being changed daily (30 mL/specimen at 37° C.) to investigate the effect of PLS immersion on physicochemical properties. DTS values (standard uncertainty equals 5%) were measured on a Universal Testing Machine (United Calibration Corp, Garden Grove, Calif.) using a loading rate of 10 mm/min, Hardening time measurements: The Gilmore needle method (standard uncertainty equals 5%) was used to measure hardening time on samples prepared as described above for DTS measurements. All samples exhibited short hardening times. The hardening times were as shown in Table 2.

TABLE 2

| Premixed Paste | HT (minutes, mean ± standard deviation, n = 3) |
|---|---|
| P1 | 10 ± 1 |
| P2 | 15 ± 1 |
| P3 | 20 ± 1 |
| P4 | 20 ± 1 |
| P5 | 35 ± 1 |
| P6 | 15 ± 1 |
| P7 | 25 ± 1 |
| P8 | 35 ± 1 |
| P9 | 20 ± 1 |

Assessments of hydroxyapatite formation: Powder X-ray diffraction ("XRD") analysis was used to estimate the extent of paste conversion to HA. The estimated standard uncertainty in 2θ measurements is 0.01° and the minimum mass fraction of a calcium phosphate phase that can be detected by XRD is about 3%.

Diametral Tensile (DTS) Strength

DTS of some of the premixed paste samples were determined as given in Table 3.

TABLE 3

| Paste | 1-day DTS (MPa) | 7-day DTS (MPa) |
|---|---|---|
| P1 | 4.3 ± 0.3 (n = 5) | 3.8 ± 0.3 |
| P2 | 3.1 ± 0.5 | 3.0 ± 0.3 |
| P3 | 2.3 ± 0.4 | 2.7 ± 0.3 |

Hydroxyapatite ("HA") Formation: Conversion of the initial cement compositions to HA was incomplete in 1-day samples. Complete and near complete conversion of the initial cement compositions to HA was found in all 7-day samples of premixed pastes using XRD.

In sum, formation of a bone replacement or dental replacement paste results by combining dry powder constituents, characterized by their conversion-to calcium complexes in the presence of carboxylic acids and water. A gelling agent, such as hydroxypropyl methyl cellulose, can be mixed with the powder to improve the cohesiveness of the paste. The ratio of combined constituents is broad and the resulting paste can be formulated to control rather precisely the physical properties of the paste, including injectability, porosity and hardening time.

While particular embodiments of the present invention have been described and illustrated, it should be understood that the invention is not limited thereto as modifications may be made by persons skilled in the art. The present application contemplates any and all modifications that fall within the spirit and scope of the underlying invention disclosed herein.

What is claimed is:

1. A method of preparing a paste for bone and tooth restoration, said method comprising the following steps:
   (a) formulating a composition of components by mixing in a substantially anhydrous condition:
   (i) a powdered calcium compound in the form of selectively sized powder particles, said particle size in the range of about 1 μm to 50 μm, said particles comprising a calcium compound selected from the group consisting of monocalcium phosphate monohydrate, monocalcium phosphate anhydrous, dicalcium phosphate anhydrous, dicalcium phosphate dehydrate, octacalcium phosphate, a-tricalcium phosphate, B-tricalcium phosphate, amorphous calcium phosphate, calcium deficient hydroxyapatite, non-stoichiometric hydroxyapatite, tetracalcium phosphate, $CaSO_4$, $CASO_4.0.5H_2O$, $CASO_4.2H_2O$, CaO, $Ca(OH)_2$, $CaCO_3$ and mixtures thereof;
   (ii) a carboxylic acid for accelerating hardening of said composition when said composition is exposed to water at a delivery site, said acid comprising an acid selected from the group consisting of glycolic, citric, tartaric, malonic, malic, maleic acids and combinations thereof;
   (ii) a non-toxic, non-aqueous water-miscible liquid; and
   (iii) a gelling agent; said powder to liquid mass ratio is at least about 1.5, said components blended to obtain a substantially homogeneous formable anhydrous paste mixture having a hardening time of less than about 35 minutes and a diametral tensile strength (DTS) in the range of about 2.7 to 3.8±0.3 MPa within seven days after hardening; and (b) storing said paste mixture under substantially anhydrous conditions.

2. The method of claim 1 wherein the gelling agent is selected from the group consisting of hydroxyl methyl cellulose, carboxymethyl cellulose, chitosan, collagen, gum, gelatin, alginate, and combinations thereof.

3. The method according to claim 1 wherein said miscible liquid is selected from the group consisting of glycerin, propylene glycol, poly(propylene glycol), poly(ethylene glycol) and mixtures thereof.

4. The method of claim 1 wherein the powder particle to liquid mass ratio is in the range of about 1.5 to 3.0.

5. The method of claim 1 wherein said non-toxic, non-aqueous water-miscible liquid is selected from the group consisting of glycerin, propylene glycol, poly (propylene glycol), poly(ethylene glycol) and mixtures thereof; and said gelling agent is selected from the group consisting of hydroxyl methyl cellulose, carboxymethyl cellulose, chitosan, collagen, gum, gelatin, alginate and combinations thereof.

* * * * *